(12) United States Patent
Carson et al.

(10) Patent No.: US 6,796,436 B2
(45) Date of Patent: Sep. 28, 2004

(54) METHOD AND APPARATUS FOR PREPARING PURE WATER

(75) Inventors: William W. Carson, Hopkinton, MA (US); Keith J. Sims, Wayland, MA (US); Bernard Mack, Natick, MA (US); Robert J. Ritz, Phoenix, AZ (US); William C. Whitehill, Chandler, AZ (US)

(73) Assignee: Ionics, Incorporated, Watertown, MA (US)

( * ) Notice: Subject to any disclaimer, the term of this patent is extended or adjusted under 35 U.S.C. 154(b) by 174 days.

(21) Appl. No.: 10/202,354

(22) Filed: Jul. 24, 2002

(65) Prior Publication Data

US 2003/0019818 A1 Jan. 30, 2003

Related U.S. Application Data

(60) Provisional application No. 60/307,781, filed on Jul. 25, 2001.

(51) Int. Cl.[7] .............................. B01D 15/00; C02F 1/18
(52) U.S. Cl. ........................ 210/501; 210/764; 210/766; 422/26; 422/27; 422/28
(58) Field of Search ................................ 210/501, 764, 210/766, 752, 754, 756, 760, 143, 169, 192, 199, 206; 422/26, 27, 28

(56) References Cited

U.S. PATENT DOCUMENTS 4,035,301 A * 7/1977 Armstrong ................. 210/220
4,462,965 A * 7/1984 Azuma et al. ........ 422/186.08
4,804,478 A * 2/1989 Tamir ......................... 210/752
4,874,435 A   10/1989 Caracciolo
4,898,679 A * 2/1990 Siegel et al. ................ 210/752
5,053,140 A * 10/1991 Hurst ......................... 210/704
5,552,057 A   9/1996 Hughes et al.
5,759,489 A   6/1998 Miura et al.
5,897,832 A   4/1999 Porter
5,928,516 A   7/1999 Hopkins et al.
6,132,628 A   10/2000 Barak
6,277,288 B1   8/2001 Gargas
6,337,020 B1 * 1/2002 Thieblin et al. ............ 210/627
6,403,031 B1 * 6/2002 Escude et al. ............... 422/28
6,444,129 B1   9/2002 Collins

* cited by examiner

*Primary Examiner*—Duane Smith
*Assistant Examiner*—Minh-Chau T. Pham
(74) *Attorney, Agent, or Firm*—David Silverstein Andover-IP-Law

(57) ABSTRACT

Water treatment systems or assemblies are normally tested after construction, at least for leaks, prior to shipping or storage. Pressure testing with a gas is hazardous, so testing with water is a standard method. After testing, the water is displaced from the system by draining or gas phase flushing. It is nearly impossible to remove all of the water from the system or assembly. This remaining water provides an environment for biological growth which contaminates the system or assembly over time. The purpose of this invention is to eliminate or minimize this biological contamination by adding a biocidal agent to the system or assembly before sealing it for shipment or storage.

40 Claims, 2 Drawing Sheets

METHOD AND APPARATUS FOR PREPARING PURE WATER

This application claims benefit of 60/307,781 filed on Jul. 25, 2001.

BACKGROUND

The present invention pertains to methods of preparing water treatment equipment for shipping and/or storage. The invention also pertains to the treatment of water, and to methods of setting up and commissioning water treatment plants. Such water treatment equipment may include, but is not limited to pressure vessels, carbon columns, ion exchange columns, ultrafiltration modules or assemblies, microfiltration modules or assemblies, nanofiltration modules or assemblies, reverse osmosis modules or assemblies, and associated pumps, conduits, valves, and instrumentation.

Modern water treatment plants are usually built in transportable size modules, e.g., in assemblies of several basic treatment units and their supporting equipment, that may be packaged on "skids" or in "trailers" for shipment to a final site for installation. These modules are usually tested before shipping. One common test is a hydrostatic pressure test. For this test the interior liquid holding volume of the module, including all piping, is filled with water and is pressurized to test for leakage and the equipment's ability to withstand pressures above normal rated design operating pressure. Quality assurance testing of the system or assembly, including operational performance testing of some components may also be performed. For example, the operational performance of an electrodialysis stack, or the pressure and response performance of pumps and other units, may be checked. After testing, the equipment is drained and/or flushed with gas, usually air, to force out as much liquid as possible. The equipment may also be partially disassembled, e.g., broken down into smaller, more transportable sub-units.

It is, however, extremely difficult, if not impossible, to remove all water from the system or assembly. Traces of water therefore remain; this may include ponded water in dead end legs of the plumbing or in crannies of the active treatment modules. This residual water may provide an environment that supports the growth of microorganisms, particularly bacteria, fungi, and molds, including biofilms, e.g., slime-enclosed colonies of microorganisms.

Normally equipment is shipped in this wetted condition and, if any sterilization and/or disinfection of the system or assembly is later needed, it is usually performed after final installation of the equipment at its destination. The interval between the completion of testing and completion of equipment installation at an intended treatment plant provides substantial time in which biological growth and/or spread of biological contamination may occur in the system or assembly. The resulting growth can make it difficult to sterilize the equipment in preparation for use in the production of treated water, particularly if biofilms have grown. As a result, it may be necessary to perform aggressive cleaning of the equipment, and perhaps to also implement a number of rather time-consuming safeguards, such as isolating certain components during cleaning, before the treatment apparatus is allowed to operate in its intended use.

That is, water treatment equipment, broadly defined, is frequently fabricated off-site, at a location other than the intended end use site, is tested at the fabrication site to some extent, and then is shipped, or is partly disassembled into shippable modules or sub-assemblies, each of which can be transported on a highway trailer or in an ocean-going container. Typically, important modules or sub-assemblies are tested with water or an aqueous solution, and several modules may be connected together during the testing procedure. The advantage of testing off site is that a dedicated test site can typically perform testing and troubleshooting more cheaply and more effectively than is possible at a remote construction site.

However, as a trade-off, before final testing and acceptance of the completed treatment plant by the end user, a system must pass through many stages, which generally comprise the following:

i. assembly or "pre-fabrication" of a treatment unit at the off-site facility ii. testing of the treatment unit at the off-site facility;

iii. preparing the unit for shipping or storage;

iv. optionally, storing the unit prior to shipment;

v. shipping the unit;

vi. storing the unit at the end user site before assembly into a complete treatment system;

vii. assembly of several units into a complete plant; and viii. sanitization and testing before acceptance by the end user.

The required degree of sanitization may vary greatly depending on the intended end use. However, for economic reasons, one would like to make the on-site sanitization, including whatever degree of disinfection or sterilization may be required, as quick and as straightforward as possible.

SUMMARY OF THE INVENTION

The present invention provides a method that eliminates or minimizes growth of microorganisms in a treatment system or assembly intended for purification of water or other liquids, during storage and/or shipping of the assembly prior to use. The method assures that the treatment equipment may be shipped, stored, and then set up or commissioned without lengthy cleaning operations in the completed treatment plant at the end-user site. The invention also includes a method of providing a treatment plant, and purifying water using equipment that has been sterilized, shipped, and stored in an aseptic state prior to end user site assembly.

Practice of the invention includes a step of providing a sterilizing condition prior to shipping or storage. This is done by introducing a biocidal agent to interior regions or fluid-containing volumes of the system for a biocidally effective level or residence time, e.g., effective, for example, to sanitize the equipment, for example, to bring about substantially 100 percent kill of microorganisms in the system or components. The method also includes the step of effectively sealing shippable units of the system or assembly against subsequent ingress of additional microorganisms.

In one embodiment of the invention, a biocidal agent is added directly to fluid that is used to test the water treatment system or assembly to provide a substantially 100 percent kill of microorganisms in the system or assembly. A substantially 100 percent kill, as used herein, means a bacteriologically significant level of kill. The level may be high, e.g., at least 99%, and is preferably a level of kill that is effective to completely eliminate viable microbial growth such that colonies of microbes do not form, or are not detected by relevant assays, during the period before final installation of the tested equipment. Preferably, water used for testing the system or assembly is treated so that it is sterile, thereby preventing introduction of live microorganisms. The water may, for example, be pretreated by means of sterile filters, passage through an effective ultraviolet light sterilization device, passage through a silver impregnated carbon column, or similar treatment prior to passage through the equipment. For ultrapure water treatment systems, preferred biocidal agents are selected from the group consisting of heat (e.g., in the form of a heated fluid), ozonated water, ozone, and hydrogen peroxide, all of which leave no residue and thus do not contaminate an ultrapure water system or assembly. Alternatively, for some embodiments of this invention, radiation treatment, such as gamma radiation, may be used as an effective biocidal agent. For drinking water treatment systems, a biocidal agent that leaves no toxic residue, or one that may be flushed out with clean water, may be used. For commercial and industrial water treatment systems or assemblies, a biocidal agent that is compatible with the end use of the water, or a biocidal agent that is easily flushed out with clean water may be used. After the system or assembly is disinfected in accordance with this invention, the disinfecting liquid is drained from the system, and ingress by microorganisms is effectively blocked by closing system openings, e.g., with microporous diaphragms or filters to seal the system.

In another preferred embodiment, liquid used to test the system or assembly may be displaced and another fluid which is or which contains a biocidal agent, may be provided to fill the system. Where high temperature is the biocidal agent, liquid or fluid at an elevated temperature may be recirculated in a closed loop throughout the system for an adequate time/temperature history in all parts of the system, to insure an effective level of kill of microorganisms. After the system or assembly is disinfected in accordance with this invention, the fluid is preferably removed from the system, at least in part, and the system is effectively sealed against ingress of microorganisms.

In another preferred embodiment, a biocidal and/or biostatic agent may be introduced to the system or assembly in the form of a gas mixture. This mixture may be used to displace liquid used for testing the system or assembly. After the system or assembly is filled with the gas phase mixture, any means of ingress by microorganisms is effectively sealed.

In another preferred embodiment, the biocidal/biostatic agent is introduced to the liquid used to test the system so that sanitization occurs during testing. The liquid and agent are then displaced by introducing gas via sterile valve(s). The gas may itself be sterile, or may be introduced using a sterile filter and appropriate sterile vent(s), so as to prevent recontamination of the system or assembly by microorganisms. After the system or assembly is sterilized in accordance with this invention, any means of ingress by microorganisms is effectively sealed. Sterile valve assemblies and sterile vent assemblies are well known in the food and beverage, pharmaceutical, and biotechnology processing industries. Examples of such sterile valves are Tri-Flo® valves manufactured by Tri Clover Incorporated. Examples of sterile vents are Aervents® filters manufactured by Millipore Corporation.

In another preferred embodiment, test liquid is drained from the system and the system is flushed with another liquid containing biocidal and/or biostatic agent. After system sterilization in accordance with this invention, liquid is displaced by means of sterile valves and aseptic gas (e.g., gas passed through an appropriate sterile filter.) After the system or assembly is thus sterilized, any means of ingress by microorganisms is effectively sealed. Some or all of the sealing devices, such as sterile vents or the like, may be installed prior to the sterilization and flushing steps.

In still another preferred embodiment, the test fluid is displaced from the system by means of sterile valves and aseptic gas introduced by means of sterile vents. Such gas may be, for example, a mixture of a gas such as air, nitrogen, argon, carbon dioxide, etc. and a gas or vapor phase biocidal agent. After the system or assembly is sterilized, any means of ingress by microorganisms is effectively sealed, preferably with an aseptic seal.

In yet another preferred embodiment, where a system is to be assembled from multiple assemblies, each assembly being of an easily shippable size, and the assembled system is tested prior to storage or shipment, sterile filters may be placed at each junction between assemblies such that after the system is sterilized, the assemblies may be separated in such a way that the sterile filters remain on each opening of each assembly, thereby preventing recontamination of the assemblies by microorganisms while allowing separate shipment and storage of each assembly.

In another preferred embodiment, the biocidal agent is selected from the group consisting of water containing ozone at a concentration ranging from about 0.0001 mg/L to 12 mg/L: ozone at a concentration ranging from about 0.1 micrograms/L to 2 weight percent of the liquid; hydrogen peroxide at a concentration ranging from about 10 mg/L to 10 weight percent of the liquid; peracetic acid at a concentration ranging from about 10 micrograms/L to 10 weight percent of the liquid: and an alkali hypochlorite at a concentration ranging from about 0.1 mg/L to 10 weight percent of the liquid.

In another preferred embodiment, the biocidal agent is selected from the group consisting of iodine, pyrrolidone-iodine, and similar iodine-organic complexes an oligodynamic metal such as silver, copper, or zinc, and mixtures thereof.

In another preferred embodiment the biocidal agent is selected from the group consisting of biocidal agents consisting of ozone at a concentration ranging from about 1 part per trillion to 10 volume percent of the gas or vapor mixture used to sterilize the system or assembly; ethylene oxide at a concentration ranging from about 1 part per trillion to 10 volume percent of the gas or vapor mixture used to sterilize the system or assembly; chlorine at a concentration ranging from about 1 part per trillion to 10 volume percent of the gas or vapor mixture used to sterilize the system or assembly; chlorine dioxide at a concentration ranging from about 1 part per trillion to 10 volume percent of the gas or vapor mixture used to sterilize the system or assembly; bromine at a concentration ranging from about 1 part per trillion to 10 volume percent of the gas or vapor mixture used to sterilize the system or assembly: chlorine monoxide at a concentration ranging from about 1 part per trillion to 10 volume percent of the gas or vapor mixture used to sterilize the system or assembly; bromine chloride at a concentration ranging from about 1 part per trillion to 10 volume percent of the gas or vapor mixture used to sterilize the system or assembly; sulfur dioxide at a concentration ranging from about 1 part per trillion to 10 volume percent of the gas or vapor mixture used to sterilize the system or assembly: and mixtures or combinations thereof.

The invention also provides a method of treating water, or of providing a treatment plant for purifying water, wherein the method includes the steps of assembling and testing modules and assemblies of an intended plant at a fabrication site, testing of at least some of the modules and sanitization and sealing thereof, followed (in any order) by storage and by transportation to a use site, and thereafter assembling the modules and assemblies into a treatment plant and operating the plant to treat water.

In a preferred embodiment of this aspect of the invention, the said water treatment plant or unit is a member of the group including: filtration, activated carbon filtration, ultraviolet irradiation, absorption, adsorption, ion exchange, electrodialysis, electrodialysis reversal, filled cell electrodialysis, electrodeionization reversal, electrodiaresis, microfiltration, membrane filtration, ultrafiltration, nanofiltration, reverse osmosis, hyperfiltration and their equivalents.

BRIEF DESCRIPTION OF THE DRAWINGS

These and other features of the invention will be understood from the description and claims herein, taken together with the drawings showing details of construction and illustrative embodiments, wherein:

DETAILED DESCRIPTION

Figure 1:
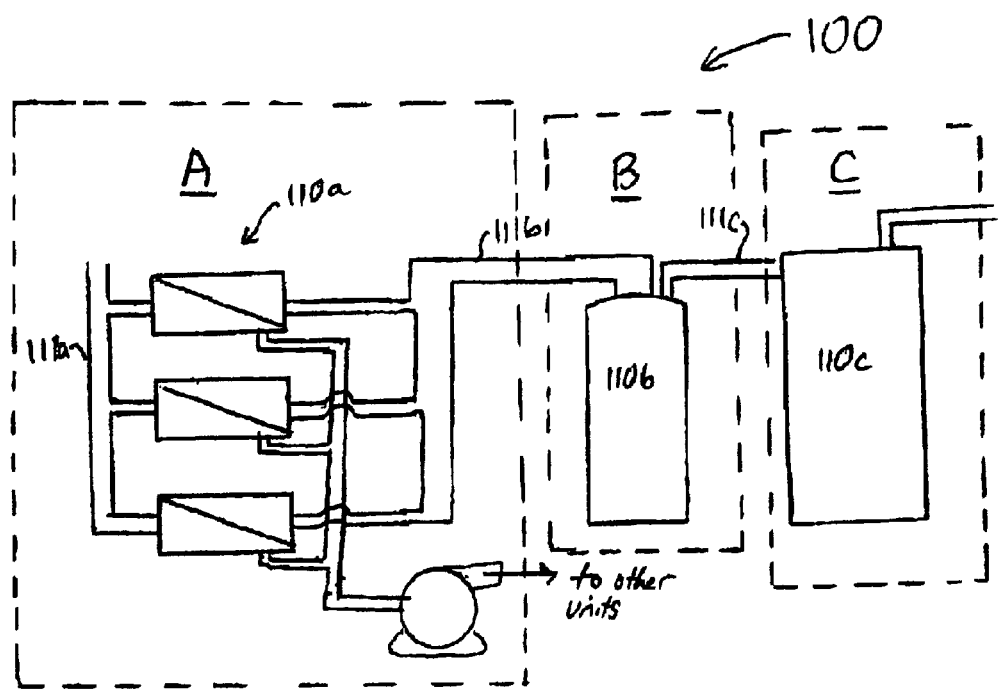
FIG. 1 schematically illustrates water treatment apparatus showing the context of the invention.

FIG. 1 illustrates liquid treatment equipment 100, which, as described more fully below, may be prepared and/or used in accordance with the present invention. As shown in FIG. 1, equipment 100 is comprised of one or more units 110a, 110b, 110c—illustratively, several units, interconnected by conduits 111a, 111b, 111c, together with related components such as pumps, meters or sensors, and the like. The units 110 may be units such as banks of reverse osmosis or other filtration cartridges, electrodialysis or electrodeionization units, exchange beds, softeners, pervaporation units, gas transfer membrane units, degasifiers, chemical storage tanks or other treatment units, as well as pumps and related equipment. These are assembled and subjected to wet testing, such as hydrostatic testing for leakage and for vessel strength, or testing to verify operational performance of the units. Illustratively, prior to shipment, larger units may be broken down into smaller subassemblies that are shippable. In FIG. 1, such shippable subassemblies are denoted by groupings A, B and C within dashed-line boxes. In accordance with a principal aspect of the invention, units are prepared for shipping by sterilization or disinfection of their interior volume, and the units are sealed and shipped in an aseptic condition.

Figure 2:
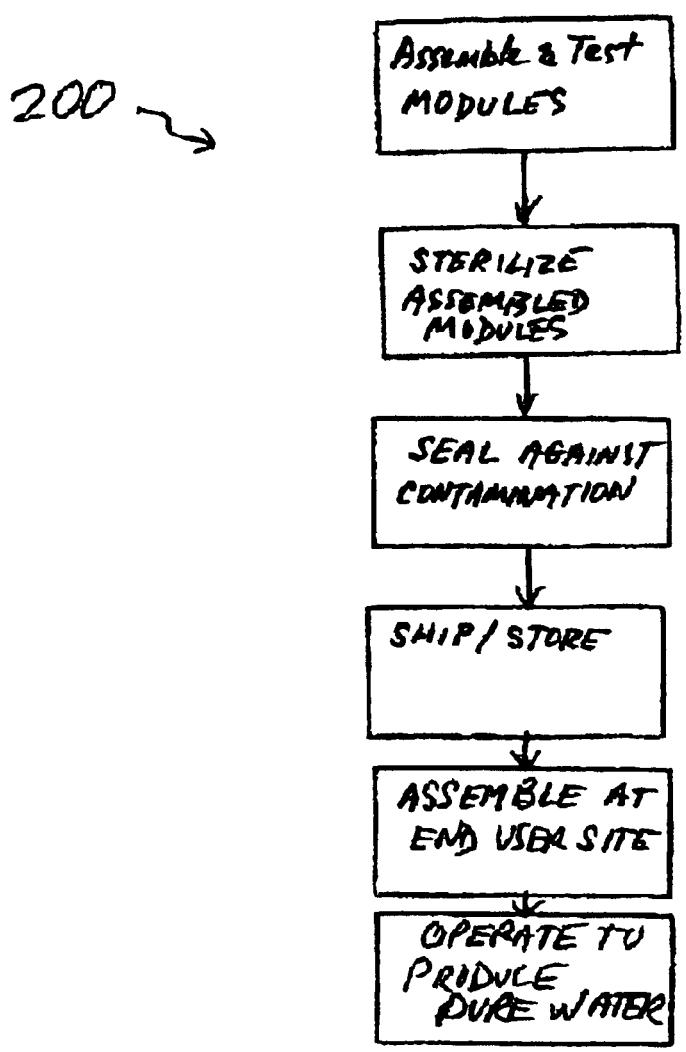
FIG. 2 schematically illustrates steps of a process of the present invention.

FIG. 2 illustrates the process 200 of the present invention for providing a treatment plant. The plant and units will be generally described with reference to water treatment and purification. However, the invention is also applicable to, and includes, treatment units for food material, sweeteners, pharmaceuticals, fine chemicals and cosmetics. As shown, equipment 100 (FIG. 1) comprised of one or more units assembled into a testable assembly is tested by a test that involves wetting or filling with water, aqueous solution, or other liquid. The assembly is then substantially sterilized. Sterilization may be effected with heated water or an aqueous solution, with radiation, or with biocidal or biostatic aqueous solution, biocidal or biostatic gas or mixtures thereof. Such sterilization may be effected at the same time as testing is performed, or may be tested afterward, with a separate flow or treatment. For example, when the testing is simple hydrostatic pressure testing, the testing may be performed with ozonated water or with a peroxide solution. In other situations, however, the testing may be performed and the test solution drained or displaced, with a biocidal agent then pumped to the interior of the treatment units. Rinses may be effected prior to active sterilization. In that case, the rinse water is preferably treated to remove microorganisms (e.g., by ultrafiltration or other suitable removal process), and is preferably also treated to remove any small molecular species that may figure in the metabolic pathways of microorganisms. Thus, rinse water or biocidal solution is preferably treated to be free of methanol, amines, nitrate and nitrite, urea, TOC residual and the like. This assures that moisture remaining in the device and pooled in dead-end regions does not itself contribute to creation of culture conditions for microorganisms within the treatment unit. Suitable sterility and purity of the treatment (rinse or biocidal) water may be obtained by suitable cross-flow or dead-ended microfilters or ultrafilters, UV irradiation at suitable wavelength and intensity, passage through a silver activated carbon bed and other such measures.

In general, applicant contemplates that at least some components of a tested system—particularly those containing RO membranes, electrodialysis membranes and/or ion exchange resins—will not be dried but will remain wetted after testing. In this case, and whenever the nature of the equipment is such that one cannot be sure that all dead ends, joints and crevices are dry, then the method of the present invention preferably includes a step of sealing the interior of decontaminated equipment from the outside world in a manner effective to prevent entry of viable contaminants.

The degree of decontamination required for a boiler feed water application will be different than that required for a pharmaceutical grade treatment plant that prepares water for compounding injectable medications. Similarly, the degree of decontamination required for a unit that is to be shipped and stored in a refrigerated container will be less than that required for a skid or trailer that is to be shipped under non-refrigerated conditions or stored in the deserts of Saudi Arabia.

A dilute mixture of ozone in water or in moist air is one preferred decontaminant. If portions of the equipment are dry, then preferably the equipment, or those parts of the equipment, are re-wetted for some hours before ozone treatment. However, the short halflife of ozone makes it less than effective when portions of the equipment interior are protected by ponded water, organic residues or the like. Circulation of ozonated water for an extended period may be necessary to attain a level of kill that is effective to prevent bacterial growth over the period of weeks or months until plant commissioning.

Other disinfectants include substances such as chlorine, triiodide, hypochlorites, chlorine dioxide, N-chloramines, iodine and polyvinyl pyrrolidone-iodine complex. Some of these may be ineffective against some microorganisms at practical concentrations. Alcohols, such as methanol and isopropanol, may be effectively employed against most microorganisms. These agents are bactericidal, fungicidal and viricidal, and act rapidly, leaving no residue. While less effective against spores, that weakness is not critical for most water treatment applications. Thus, by flushing with alcohol and then sealing, equipment 100 may be suitably prepared for shipment, extended storage and ultimate reassembly or commissioning.

A number of conventional biocidal formulations such as phenolic or diphenyl compounds and bisphenols may be utilized, as well as acids such as hydroxy benzoic acid or its esters (e.g., the parabens), sorbic acid (2,4 hexadienoic acid), glutaric acid, various aldehydes (such as a 7% formaldehyde solution or vapors in air), glutaraldehyde (but this should not be used on some types of RO membrane), various sulfur compounds, and other disinfectants or biostatic agents. In addition, certain treatments of known effectiveness for particular units may be applied to specific portions of the shippable systems, such as a mixture of 18% propylene glycol (and/or glycerine) and 1% sodium bisulfite applied for long term storage or shipment of certain RO membrane units, triiodide, e.g. with propylene glycol or other polyol in EDR stacks, and alkali carboxylic biocides such as pH4 sodium benzoate or sodium sorbate for UF and RO elements. Alkali percarbonates and perborates may also be used, as well as chloramines and common biocides effective for RO membranes, such as octly isothiazolin or DBNPA (dibromonitrilopropylamine).

The choice of disinfectant may depend on the specific treatment units constituting a shippable module. Activated carbon beds, for example, may be effectively disinfected with steam, but cannot be readily sterilized with chlorine or hypochlorite, or with biocidal or biostatic organic compounds. On the other hand, most RO membranes will not tolerate steam sterilization, but are readily treated with certain organic agents.

Following disinfection, the system is aseptically flushed or purged. This may be done with a gas that is also a disinfectant or biocide, or in some embodiments a biocidal gas may be introduced or circulated after the disinfecting liquid is substantially drained. For example, ozone may be introduced following the circulation and removal of a water/peroxide disinfectant. Following disinfection, aseptic seals are also added, if not already present, to assure that the shippable modules are protected against ingress of further microorganisms. The effectively sterilized, sealed units are then optionally stored, locally or at a distribution center, transported, generally stored at an intended use site, such as the plant construction or assembly site, before final installation and commissioning for water purification. Modules and assemblies treated in accordance with the present invention are then readily placed in service at the intended use site and operated to purify water without requiring aggressive cleaning or sanitization, and without risk of instigating biological fouling of related or connected membranes and components.

In addition to the sterilization and preparation of equipment at a fabrication site prior to storage, shipping, remote storage and ultimately installation at an end user site, the invention may be applied to prepare used equipment, for example a skid or trailer that is already in the field, prior to the equipment being taken out and set up at a different field site.

Advantageously, the methods described herein allow treatment modules and other equipment to be dependably transported and stored for lengthy periods of time, and to be set up and placed in use to purify or treat water or other intended liquid at an end user site with little or with very simple cleaning. As such, the method substantially avoids occurrences of biofouling and underperformance of equipment, or the complications of unanticipated or unknown sources of biofouling.

The Specification has disclosed several embodiments of this invention, and although specific terms are employed, they are used in a generic and descriptive sense only and not for the purposes of limitation. It is understood that modifications and variations thereof will naturally occur to those skilled in the art, and all such variations and modifications are considered to be within the scope of the invention as described herein and by the claims appended hereto and equivalents thereof.

What is claimed is:

1. In a method of hydrostatic pressure-testing a transportable-sized water treatment module by flowing a test fluid into, through, and out of said module, optionally followed by passing a flushing liquid into, through, and out of said module to flush remaining test fluid from the module, and of preparing the hydrostatic pressure-tested module for storage and/or shipping, the improvement comprising the steps of:

(a) introducing a biocidal agent into at least a portion of the test fluid being fed to the module to hydrostatic pressure-test the module or into at least a portion of the flushing liquid being fed to the module to flush test fluid from the module to prepare a hydrostatic pressure-tested and biocidally-treated module;

(b) displacing at least a portion of the liquid containing said biocidal agent from the hydrostatic pressure-tested and biocidally-treated module by using a gas which has been passed through sterilizing filters; and, (c) thereafter sealing the hydrostatic pressure-tested and biocidally-treated module against biological ingress so as to maintain an aseptic condition during storage and/or shipping.

2. In a method of hydrostatic pressure-testing a transportable-sized water treatment module by flowing a test liquid into, through, and out of said module, optionally followed by passing a flushing liquid into, through, and out of said module to flush remaining test liquid from the module, and of preparing the hydrostatic pressure-tested module for storage and/or shipping, the improvement comprising the steps of:

(a) displacing a at least a portion of any liquid remaining in the module;

(b) introducing a biocidal agent comprising a mixture of gas or vapor and a biocidal gas or vapor into the module; and, (c) sealing the module against biological ingress so as to maintain an aseptic condition during storage and/or shipping.

3. A method of according to claim 1, wherein the module includes a sterile valve or drain through which the liquid or gas passes, and the step of sealing includes closing a valve or drain to seal the module against biological ingress.

4. A method according to claim 1, wherein the step of introducing a biocidal agent includes heating said portion of the test fluid or said portion of the flushing liquid to a temperature of about 50 to 100 degrees Centigrade for a period of time sufficient for the heated liquid to act as a biocidal agent to achieve an effective level of kill of any biological species that might normally be present.

5. A method according to claim 1, wherein the biocidal agent is an agent that leaves no residual contaminants in the module.

6. A method according to claim 5, wherein the biocidal agent is selected from the group consisting of water containing ozone at a concentration ranging from about 0.0001 mg/L to 12 mg/L; ozone at a concentration ranging from about 0.1 micrograms/L to 2 weight percent of the liquid; hydrogen peroxide at a concentration ranging from about 10 mg/L to 10 weight percent of the liquid; peracetic acid at a concentration ranging from about 10 micrograms/L to 10 weight percent of the liquid; and an alkali hypochlorite at a concentration ranging from about 0.1 mg/L to 10 weight percent of the liquid.

7. A method according to claim 1, wherein the biocidal agent is selected from the group consisting of iodine, pyrrolidone-iodine, and similar iodine-organic complexes, an oligodynamic metal such as silver, copper, or zinc, and mixtures thereof.

8. A method according to claim 2, wherein the biocidal agent comprises a gas or vapor heated to a temperature of 50 to 100 degrees Centigrade and is present in the module for a period of time sufficient to effect a substantially 100% kill of any biological species that might normally be present.

9. A method according to claim 8, wherein the biocidal agent is selected from among the group of biocidal agents consisting of ozone at a concentration ranging from about 1 part per trillion to 10 volume percent of the gas or vapor mixture used to sterilize the system or assembly; ethylene oxide at a concentration ranging from about 1 part per trillion to 10 volume percent of the gas or vapor mixture used to sterilize the system or assembly; chlorine at a concentration ranging from about 1 part per trillion to 10 volume percent of the gas or vapor mixture used to sterilize the system or assembly; chlorine dioxide at a concentration ranging from about 1 part per trillion to 10 volume percent of the gas or vapor mixture used to sterilize the system or assembly; bromine at a concentration ranging from about 1 part per trillion to 10 volume percent of the gas or vapor mixture used to sterilize the system or assembly; chlorine monoxide at a concentration ranging from about 1 part per trillion to 10 volume percent of the gas or vapor mixture used to sterilize the system or assembly; bromine chloride at a concentration ranging from about 1 part per trillion to 10 volume percent of the gas or vapor mixture used to sterilize the system or assembly; sulfur dioxide at a concentration ranging from about 1 part per trillion to 10 volume percent of the gas or vapor mixture used to sterilize the system or assembly; and mixtures or combinations thereof.

10. In a method of providing treated water, which method comprises seriatim the steps of:
  (a) providing a pre-assembled apparatus comprising:
    at least one transportable-sized water treatment unit for carrying out at least one water treatment unit operation, said unit having an interior portion for passing and heating treating water;
    at least one water inlet conduit in fluid communication with at least one fluid entrance to said water treatment unit, said inlet conduit having an interior portion for passing water; and
    at least one water outlet conduit in fluid communication with at least one fluid exit from said treatment unit, said outlet conduit having an interior portion for passing water;
  (b) testing the water treatment unit for leaks by passing a test fluid into said unit;
  (c) transporting said water treatment unit during a transport time period in a transport temperature range;
  (d) providing a first stream of water to said water inlet conduit;
  (e) passing said first stream of water seriatim through said interior portion of said water inlet conduit, through said interior portion of said water treatment units and through said interior portion of said water outlet conduit thereby providing treated water; and,
  (f) recovering treated water from said apparatus;
  the improvement comprising the further step of: prior to carrying out step (c), passing a second fluid into the interior of said water treatment unit to flush test fluid, wherein at least a portion of said second fluid contains a biocidal agent, or has been treated or selected to be essentially free of viable micro-organisms, or both.

11. A method of providing treated water according to claim 10, wherein said second fluid is passed through said interior portion of said inlet conduit and/or through said interior portion of said outlet conduit into said interior portion of said treatment unit.

12. A method of providing treated water according to claim 11, wherein said second fluid is essentially free of viable micro-organisms.

13. A method of providing treated water according to claim 11, wherein said second fluid is essentially free of organic compounds other than biocidal and/or biostatic agents.

14. A method of providing treated water according to claim 11, wherein said second fluid contains at least one biocidal and/or biostatic agent, and at least a portion of said second fluid remains in said interior portion of said water treatment unit for at least a predetermined time period within a predetermined temperature range such that said portion contains at least one biocidal and/or biostatic agent at a concentration effective to achieve biocide and/or biostasis in said interior portion.

15. A method of providing treated water according to claim 10, wherein said water treatment unit is a member of the group including: filtration, activated carbon filtration, ultraviolet irradiation, absorption, adsorption, ion exchange, electrodialysis, electrodialysis reversal, filled cell electrodialysis, electrodeionization reversal, electrodiaresis, microfiltration, membrane filtration, ultrafiltration, nanofiltration, reverse osmosis, hyperfiltration and their equivalents.

16. A method of providing treated water according to claim 10, further including, between steps (b) and (c), the step of storing said water treatment unit for a first storage time in a first predetermined storage temperature range selected to inhibit growth of microorganisms during said first storage or transport time.

17. A method of providing treated water according to claim 10, wherein said improvement comprises a biocidal and/or biostatic process.

18. A method of providing treated water according to claim 10, wherein said water treatment unit includes a component for aseptically isolating said interior portion, said component comprising a gas-permeable component selected from among the group of elements including microporous diaphragms, sterile vents, sterile valves and their equivalents.

19. A method of providing treated water according to claim 10, wherein said transport temperature range of step (c) is selected to inhibit growth of microorganisms during said transport time period.

20. A method of providing treated water according to claim 10, wherein said water treatment unit comprises a module and wherein said method comprises displacing test fluid from said module, introducing a biocidal and/or biostatic agent comprising a mixture of gas and/or vapor with at least one biocidal and/or biostatic gas and/or vapor into said module, and sealing the module against biological ingress.

21. A method of providing treated water according to claim 10, wherein said water treatment unit comprises a module and wherein said method comprises introducing a biocidal and/or biostatic agent into the test fluid and/or into the second fluid used to flush said test fluid from said module, displacing said test fluid or said flush fluid from said module by a sterile fluid, and sealing said module against biological ingress.

22. A method according to claim 20 wherein said module includes a sterile valve or drain through which fluid passes, said method further comprising the step of sealing said module against biological ingress by closing said valve or drain.

23. A method of providing treated water according to claim 10, further comprising the step of maintaining the apparatus at a temperature of from about 50 degrees Centigrade to about 100 degrees Centigrade for a period of time sufficient to achieve an effective level of kill of any biological species that might normally be present in the apparatus.

24. A method according to claim 2, wherein the module includes a sterile valve or drain through which the liquid or gas passes, and the step of sealing includes closing a valve or drain to seal the module against biological ingress.

25. A method according to claim 2, wherein the step of introducing a biocidal agent includes heating said liquid to a temperature of about 50 to 100 degrees Centigrade for a period of time sufficient for the heated liquid to act as a biocidal agent to achieve an effective level of kill of any biological species that might normally be present.

26. A method according to claim 2, wherein the biocidal agent is an agent that leaves no residual contaminants in the module.

27. A method according to claim 26, wherein the biocidal agent is selected from the group consisting of water containing ozone at a concentration ranging from about 0.0001 mg/L to 12 mg/L; ozone at a concentration ranging from about 0.1 micrograms/L to 2 weight percent of the liquid; hydrogen peroxide at a concentration ranging from about 10 mg/L to 10 weight percent of the liquid; peracetic acid at a concentration ranging from about 10 micrograms/L to 10 weight percent of the liquid; and an alkali hypochlorite at a concentration ranging from about 0.1 mg/L to 10 weight percent of the liquid.

28. A method according to claim 2, wherein the biocidal agent is selected from the group consisting of iodine, pyrrolidone-iodine, and similar iodine-organic complexes, an oligodynamic metal such as silver, copper, or zinc, and mixtures thereof.

29. A method according to claim 1, wherein the biocidal agent comprises a gas or vapor heated to a temperature of 50 to 100 degrees Centigrade and is present in the module for a period of time sufficient to effect a substantially 100% kill of any biological species that might normally be present.

30. A method according to claim 29, wherein the biocidal agent is selected from among the group of biocidal agents consisting of ozone at a concentration ranging from about 1 part per trillion to 10 volume percent of the gas or vapor mixture used to sterilize the system or assembly; ethylene oxide at a concentration ranging from about 1 part per trillion to 10 volume percent of the gas or vapor mixture used to sterilize the system or assembly; chlorine at a concentration ranging from about 1 part per trillion to 10 volume percent of the gas or vapor mixture used to sterilize the system or assembly; chlorine dioxide at a concentration ranging from about 1 part per trillion to 10 volume percent of the gas or vapor mixture used to sterilize the system or assembly; bromine at a concentration ranging from about 1 part per trillion to 10 volume percent of the gas or vapor mixture used to sterilize the system or assembly; chlorine monoxide at a concentration ranging from about 1 part per trillion to 10 volume percent of the gas or vapor mixture used to sterilize the system or assembly; bromine chloride at a concentration ranging from about 1 part per trillion to 10 volume percent of the gas or vapor mixture used to sterilize the system or assembly; sulfur dioxide at a concentration ranging from about 1 part per trillion to 10 volume percent of the gas or vapor mixture used to sterilize the system or assembly; and mixtures or combinations thereof.

31. A transportable-sized water treatment apparatus which has been hydrostatic pressure-tested and aseptically prepared for storage and/or transport according to the following steps:

(a) flowing a test fluid into, through, and out of said apparatus, optionally followed by passing a flushing liquid into, through and out of said module to flush remaining test fluid from the apparatus;

(b) introducing a biocidal agent into at least a portion of the test fluid being fed to the apparatus to hydrostatic pressure-test the apparatus or into at least a portion of the flushing liquid being fed to the apparatus to flush test fluid from the apparatus;

(c) displacing at least a portion of the liquid containing said biocidal agent from the apparatus by using a gas which has been passed through sterilizing filters; and, (d) thereafter sealing the hydrostatic pressure-tested and biocidally-treated apparatus against biological ingress so as to maintain aseptic condition during storage and transport.

32. Apparatus according to claim 31 wherein the preparation of said apparatus for the storage and/or transport has included a step of passing a flushing liquid through an interior portion of the apparatus.

33. Apparatus according to claim 32 wherein said flushing liquid is essentially free of viable micro-organisms.

34. Apparatus according to claim 32 wherein said flushing liquid is essentially free of organic compounds other than biocidal and/or biostatic agents.

35. Apparatus according to claim 32 wherein said portion of said flushing liquid contains at least one biocidal and/or biostatic agent, and at least a portion of said flushing liquid containing a biocidal and/or biostatic agent remains in said interior portion of said apparatus for at least a predetermined time period within a predetermined temperature range such that said flushing liquid portion contains or acts as at least one biocidal and/or biostatic agent at a concentration effective to achieve biocide and/or biostasis in said interior portion.

36. Apparatus according to claim 31 wherein said water treatment apparatus is a member of the group including: filtration apparatus, activated carbon filtration apparatus, ultraviolet irradiation apparatus, absorption apparatus, adsorption apparatus, ion exchange apparatus, electrodialysis apparatus, electrodialysis reversal apparatus, filled cell electrodialysis apparatus, electrodeionization reversal apparatus, electrodiaresis apparatus, microfiltration apparatus, membrane filtration apparatus, ultrafiltration apparatus, nanofiltration apparatus, reverse osmosis apparatus, hyperfiltration apparatus or their equivalents.

37. Apparatus according to claim 31 wherein the preparation of said apparatus for storage and/or transport has included a step of storing said apparatus prior to transport for a first storage time in a first predetermined storage temperature range selected to inhibit growth of microorganisms during said first storage or transport time.

38. Apparatus according to claim 31 wherein the preparation of said apparatus for storage and/or transport has included a biocidal and/or biostatic process.

39. Apparatus according to claim 31 wherein said water treatment apparatus includes a component for aseptically isolating an interior portion of said apparatus, said component comprising a gas-permeable component selected from among the group of elements including microporous diaphragms, sterile vents, sterile valves and their equivalents.

40. Apparatus according to claim 31 wherein said apparatus has been transported at a temperature selected to inhibit growth of microorganisms during transport.

* * * * *